Feb. 19, 1952 A. J. MARS Plant Pat. 1,075
APPLE TREE
Filed Nov. 18, 1947
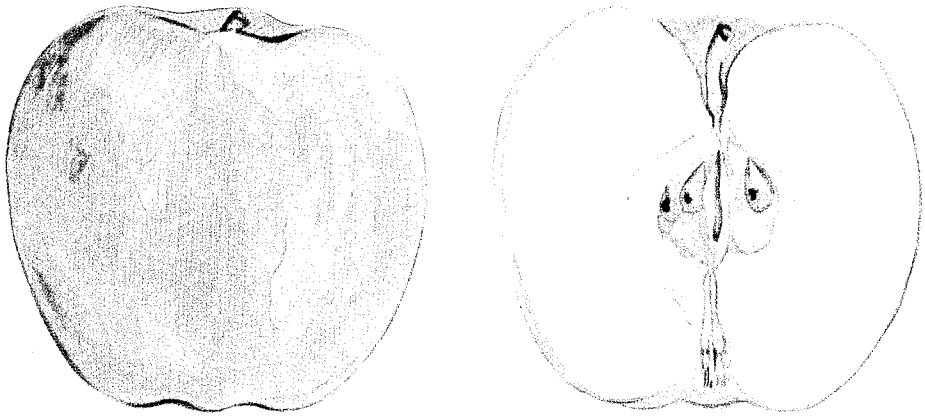
INVENTOR
Alvin J. Mars
By Orville M. Kile
Plant Pat. Agt.

Patented Feb. 19, 1952

Plant Pat. 1,075

UNITED STATES PATENT OFFICE 1,075

APPLE TREE

Alvin J. Mars, Entiat, Wash., assignor to Columbia & Okanogan Nursery Company, Wenatchee, Wash.

Application November 18, 1947, Serial No. 786,818

1 Claim. (Cl. 47—62)

My present discovery relates to a new and distinct variety of apple tree, originating in my orchards at Entiat, Washington, from crosses of two other varieties made by me on a Jonathan tree. The male parent is uncertain because identifying labels were lost from the seedlings.

The tree of my new variety is approximately like that of the Stayman Winesap in growth, form and many other features. The fruit of these two varieties appear to be similar in size and shape, except that the points on my new apple at the calyx end are usually more prominent than on the Stayman Winesap. The color of my new variety is a brighter red. The flesh of the fruit of my new variety is very different from that of Stayman Winesap, particularly in flavor which is more nearly like that of the Jonathan variety.

The early ripening date of this new variety is one of its most outstanding features. It ripens thirty to forty days earlier than Stayman Winesap and about two weeks earlier than Jonathan—at a time when there is no apple of comparable size and quality on the market, thus enabling the commercial season for this type of apple to be extended. This apple was ready to pick from the parent tree in Entiat in 1948 on September 3rd and from the adjoining Jonathan on September 18th. In the Wenatchee Valley, on a top-worked tree, the fruit of this variety was ready to pick on August 25th and Jonathans on September 10th. In 1949 the apples from the parent tree were ready to pick September 8th and the Jonathans ready about September 24th.

This tree and its fruit have never had any trace of mildew, although the Jonathan in the same orchard some seasons has lots of it and it is very hard to control.

My new variety has been reproduced by budding, both in my orchards near Entiat, Washington and at Wenatchee, Washington, and its distinguishing characteristics appear to be permanent.

The accompanying illustration shows, in approximately true colors, a side view and cross-section view of a typical fruit of my new variety. The flesh of many specimens, however, shows somewhat more yellowish color than is here depicted by the artist.

Following is a detailed description of my new variety of apple tree:

*The tree*

Size: Medium to large.
Growth: Vigorous.
Form: Spreading.
Twigs: Medium to long, moderately stout, with large terminal buds. Internodes medium in length.

Lenticels: Inconspicuous; scattered.
Bark: Very smooth; dark brown; slightly darker than that of the Jonathan variety.
Leaves: Medium in length; rather narrow.
Buds: Medium to large; pubescent; plump.

*The fruit*

Maturity season: Thirty or forty days earlier than the Stayman Winesap, which matures October to December depending on location. About two weeks earlier than Jonathan, grown under the same conditions.
Size: Medium to large.
Form: Roundish conic to globular, flattened at base and top. Sides sometimes somewhat unequal. The five points at the calyx end usually extend upward along sides of apple in form of bulges.
Cavity: Large; deep; medium in width.
Basin: Small; sometimes oblique; variable in depth and width; somewhat wrinkled.
Calyx: Small to medium.
Stem: Medium to short.
Skin: Smooth; rather thick and tough; glossy.
Color: Underlying color light green to light yellow. Usually almost covered with indistinct or broken stripes of faint red (Eosine Pink, Plate I, Ridgway's Color Standards and Nomenclature) to Carmine (Plate I), with lighter reds between the stripes, thus giving a fully red appearance on parts of the fruit, varying from one-quarter to four-fifths of the surface on different specimens. Small light-gray and russet dots are often rather conspicuous.
Flesh:
*Color.*—White to slightly yellowish.
*Texture.*—Crisp; tender; juicy; firm; moderately fine-grained.
*Flavor.*—Sprightly sub-acid; somewhat similar to that of Jonathan.
*Quality.*—Best.
Core: Small to medium; cells symmetrical; calyx tube cone-shaped; carpels thin and concave.
Seeds: Plump; medium brown; variable size.
Keeping quality: Good.

Having thus disclosed my discovery, I claim:

The new and distinct variety of apple tree substantially as herein shown and described, characterized particularly by its early ripening season; its ability to resist powdery mildew; and its fruit with Jonathan-like flavor, of about the size and shape of Stayman Winesap but with more prominent points at calyx end, and color a brighter red.

ALVIN J. MARS.

No references cited.